United States Patent
Mihailescu

(10) Patent No.: US 9,849,307 B2
(45) Date of Patent: Dec. 26, 2017

(54) SYSTEM AND METHOD FOR DOSE VERIFICATION AND GAMMA RAY IMAGING IN ION BEAM THERAPY

(71) Applicant: Lucian Mihailescu, Pleasant Hill, CA (US)

(72) Inventor: Lucian Mihailescu, Pleasant Hill, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/886,862

(22) Filed: Oct. 19, 2015

(65) Prior Publication Data

US 2016/0114189 A1 Apr. 28, 2016

Related U.S. Application Data

(60) Provisional application No. 62/066,477, filed on Oct. 21, 2014.

(51) Int. Cl.
*G21K 1/02* (2006.01)
*A61N 5/10* (2006.01)

(52) U.S. Cl.
CPC ......... *A61N 5/1048* (2013.01); *A61N 5/1045* (2013.01); *A61N 5/1071* (2013.01); *A61N 5/1084* (2013.01); *G21K 1/025* (2013.01); *A61N 2005/1087* (2013.01)

(58) Field of Classification Search
None
See application file for complete search history.

(56) References Cited

U.S. PATENT DOCUMENTS

| 7,525,593 | B2 * | 4/2009 | Ichikawa | G01D 5/347 348/187 |
| 8,049,176 | B1 | 11/2011 | Majewski et al. | |
| 2015/0297917 | A1 * | 10/2015 | Beekman | A61N 5/1043 600/1 |
| 2015/0380121 | A1 * | 12/2015 | Beekman | G01T 1/1648 378/147 |

OTHER PUBLICATIONS

V. Bom et al., "Real-time prompt gamma monitoring in spot-scanning proton therapy using imaging through a knife-edge-shaped slit," Phys. Med. Biol., vol. 57, pp. 297-308, (2012).
J. Smeets et al., "Prompt gamma imaging with a slit camera for real-time range control in proton therapy," Phys. Med. Biol., vol. 57, pp. 3371-3405, (2012).
C.H. Min et al., "Development of array-type prompt gamma measurement system for in vivo range verification in proton therapy," Med. Phys., vol. 39, pp. 2100-2107, (2012).

(Continued)

*Primary Examiner* — Edwin Gunberg

(57) ABSTRACT

This disclosure provides systems, methods, and apparatus related to ion beam therapy. In one aspect, a system includes a position sensitive detector and a collimator. The position sensitive detector configured to detect gamma rays generated by an ion beam interacting with a target. The collimator is positioned between the target and the position sensitive detector. The collimator includes a plurality of knife-edge slits, with a first knife-edge slit intersecting with a second knife-edge slit.

20 Claims, 7 Drawing Sheets

(56) References Cited

OTHER PUBLICATIONS

Dieter Schardt et al., "Heavy-ion tumor therapy: Physical and radiobiological benefits," Reviews of Modern Physics, vol. 82, Issue 1, pp. 383-426, (Jan.-Mar. 2010).
K. Parodi et al., "In-beam PET measurements of β+ radioactivity induced by proton beams," Phys. Med. Biol. vol. 47, pp. 21-36, (Nov. 29, 2001).
Roberto Accorsi et al., "Optimal coded aperture patterns for improved SNR in nuclear medicine imaging," Nuclear Instruments and Methods in Physics Research Section A: Accelerators, Spectrometers, Detectors and Associated Equipment, vol. 474, Issue 3, pp. 273-284, (Dec. 11, 2001).
K.A. Nugent et al., "Coded aperture imaging: a Fourier space analysis," Applied Optics, vol. 26, No. 3, pp. 563-569, (Feb. 1, 1987).
K. Choi et al., "Coded Aperture Computed Tomography," Proc. of SPIE, vol. 7468, pp. 746880B1-746880B10, (2009).
R. F. Marcia et al., "Compressive Coded Aperture Superresolution Image Reconstruction," IEEE International Conference on Acoustics, Speech and Signal Processing, ICASSP, vol. 2008, pp. 833-836, (2008).
M. Frandes et al., "A Tracking Compton-Scattering Imaging System for Hadron Therapy Monitoring," IEEE Transactions on Nuclear Science, vol. 57, No. 1, pp. 144-150, (Feb. 2010).
S. Kurosawa et al., "Prompt gamma detection for range verification in proton therapy," Current Applied Physics, vol. 12, Issue 2, pp. 364-368, (Mar. 2012).

* cited by examiner

SYSTEM AND METHOD FOR DOSE VERIFICATION AND GAMMA RAY IMAGING IN ION BEAM THERAPY

RELATED APPLICATIONS

This application claims priority to U.S. Provisional Patent Application No. 62/066,477, filed Oct. 21, 2014, which is herein incorporated by reference.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to ion beam therapy and more particularly to high-energy gamma ray imaging in ion beam therapy.

BACKGROUND

Radiation therapy using proton and ion beams is an effective method to treat various types of localized malignant tumors [1]. One of the main issues of using radiation for treatment is the lack of the capability to determine the dose deposited in organs in real time during the treatment. This is important to guide the treatment, to adjust the ion beam in real time so that minimal dose is delivered to sensitive organs and noncancerous tissue, to correct for the movement of the organs inside the body, and to act as a fail-safe mechanism. Over the past years, there have been several accidents with radiation treatment procedures which led to deliveries of much higher doses than planned, or radiation delivered to wrong areas, leading to fatalities. Mapping the radiation dose delivered during a treatment session is also important for the planning of future treatment sessions.

SUMMARY

One innovative aspect of the subject matter described in this disclosure can be implemented in a system including a position sensitive detector and a collimator. The position sensitive detector is configured to detect gamma rays generated by an ion beam interacting with a target. The collimator is positioned between the target and the position sensitive detector. The collimator includes a plurality of knife-edge slits, with a first knife-edge slit intersecting with a second knife-edge slit.

In some implementations, the collimator is about 1.5 centimeters to 12.7 centimeters thick. In some implementations, the collimator comprises tungsten.

Another innovative aspect of the subject matter described in this disclosure can be implemented in a system including a position sensitive detector and a collimator. The position sensitive detector is configured to detect gamma rays generated by an ion beam interacting with a target. The collimator includes a first plurality of knife-edge slits and a second plurality of knife-edge slits. The first plurality of knife-edge slits are substantially parallel to one another. The the second plurality of knife-edge slits are substantially parallel to one another. The first plurality of knife-edge slits are not parallel to the second plurality of knife-edge slits.

In some implementations, the collimator is about 1.5 centimeters to 12.7 centimeters thick. In some implementations, the collimator comprises tungsten.

Another innovative aspect of the subject matter described in this disclosure can be implemented in a method including providing a system. The system includes a position sensitive detector and a collimator. The position sensitive detector is configured to detect gamma rays generated by an ion beam interacting with a target. The collimator is positioned between the target and the position sensitive detector. The collimator includes a plurality of knife-edge slits, with a first knife-edge slit intersecting with a second knife-edge slit. Gamma rays are detected with the position sensitive detector to generate a data set. A two-dimensional image of emission of the gamma rays from the target is generated using the data set. The position of a Bragg peak of the ion beam is determined.

In some implementations, the collimator is about 1.5 centimeters to 12.7 centimeters thick. In some implementations, the collimator comprises tungsten.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventor for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Systems configured to monitor a proton beam or an ion beam in real time are described herein. Monitoring the proton beam or ion beam may be performed by the imaging of gamma-radiation that is emitted from the nuclear reactions or by the scattering of the Bremsstrahlung radiation inside the body during proton beam or ion beam treatment. Previous attempts to monitor the dose delivered by ions have used PET imaging [2]. This technique, however, has limited use for real-time monitoring due to longer decay times of the beta+emitters and low counting statistics. Embodiments of ion beam therapy dose verification systems described herein may be able to image high-energy gamma rays with high position resolution and high sensitivity. Embodiments of ion beam therapy dose verification systems described herein may also be used to map the total radiation dose delivered during a treatment session; this information may be useful in planning future treatment sessions.

Figure 1:
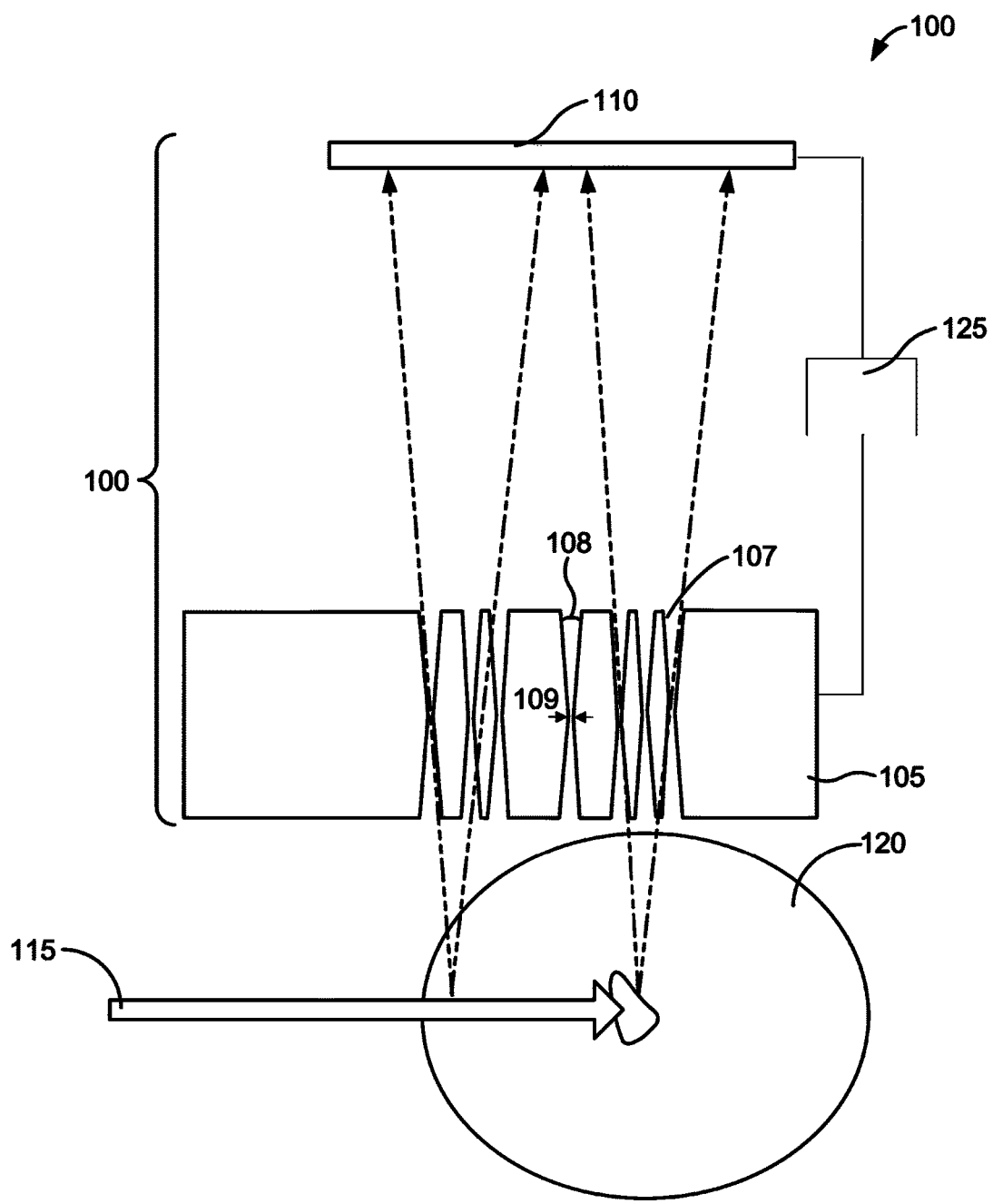
FIG. 1 shows an example of a schematic illustration of an ion beam therapy dose verification system.

FIG. 1 shows an example of a schematic illustration of an ion beam therapy dose verification system. As shown in FIG. 1, the system 100 comprises a multi-slit knife-edge collimator 105 and a position sensitive detector 110. In some embodiments, the system 100 includes a motor 125 (e.g., an electric motor) coupled to the multi-slit knife-edge collimator 105 and the position sensitive detector 110 and operable to adjust a position of the multi-slit knife-edge collimator 105 and a position of position sensitive detector 110. In some embodiments, the motor 125 is only coupled to the multi-slit knife-edge collimator 105 and is operable to adjust a position of the multi-slit knife-edge collimator 105. In these embodiments, the position sensitive detector 110 remains in place.

Also shown in FIG. 1 are an ion beam 115 and a target 120. The ion beam 115 may comprise, for example, protons or carbon atoms. The ion beam may be generated by an ion-accelerator system (not shown). The multi-slit knife-edge collimator 105 is positioned between the position sensitive detector 110 and the target 120. In some embodiments, a distance between the multi-slit knife-edge collimator 105 and the position sensitive detector 110 is larger than a distance between the multi-slit knife-edge collimator 105 and the target 120. In some embodiments, this may provide an image magnification that allows for better imaging resolution. In some embodiments, a distance between the multi-slit knife-edge collimator 105 and the position sensitive detector 110 is substantially the same as or similar to a distance between the multi-slit knife-edge collimator 105 and the target 120. In some embodiments, a distance between the multi-slit knife-edge collimator 105 and the position sensitive detector 110 and a distance between the multi-slit knife-edge collimator 105 and the target 120 are configured to be adjustable or changeable.

A knife-edge slit in a collimator is distinguished from a parallel slit in a collimator in that a parallel slit has parallel walls in the collimator. In contrast, a knife-edge slit has a wide opening on a first side on the collimator, the slit narrows in the collimator, and then the slit has a wide opening on a second side of the collimator. For example, some knife-edge slits may have a cross-section of two isosceles triangles with the vertex angle (i.e., the angle formed by legs of an isosceles triangle) of one isosceles triangle being disposed on the vertex angle of the other isosceles triangle. In some embodiments, a knife-edge slit having a cross-section of two isosceles triangles with the vertex angle of one isosceles triangle being disposed on the vertex angle of the other isosceles triangle forms a symmetrical, bow-tie shaped cross-section for the knife-edge slit. A knife-edge slit allows for a larger field of view of radiation generated by the interaction of an ion beam with a target than a parallel slit. In some embodiments, knife-edge slits in a collimator all have the same cross-section in the collimator.

Due to the differences in the amount of material of a collimator that can block radiation in a collimator having a knife-edge slit, such a collimator may permit some attenuated radiation to pass though the collimator. For example, at the narrowest portion in a knife-edge slit, a collimator has the least amount of material that can serve to block radiation. In some embodiments, the narrowest portion of the knife-edge slit is half-way though the thickness of the collimator. At this portion of a knife-edge slit and at proximal portions of a knife-edge slit, attenuated radiation may pass though the collimator.

As shown in FIG. 1, a knife-edge slit can be defined by an angle 108 of knife-edge slit. In some embodiments, the angle of a knife-edge slit is about 5° to 35°, or about 10°. In some embodiments, a dimension of the smallest width 109 of a knife-edge slit is about 0.1 mm to 4 mm.

In some embodiments, knife-edge slits 107 of the multi-slit knife-edge collimator 105 are oriented at multiple angles with respect to the direction of the ion beam 115. Each knife-edge slit 107 in the multi-slit knife-edge collimator 105 generates a one dimensional (1-D) projection of the source distribution on the position sensitive detector 110. The projection produced by each knife-edge slit may partially overlap with the projections from other knife-edge slits, creating an inverse problem similar to a coded aperture [3, 4] or a compressive sensing [5, 6] imager. An image reconstruction algorithm can be used to reconstruct a two dimensional (2-D) image of the distribution of gamma ray emissions along the ion beam path. Note that a single knife-edge slit collimator [7, 8], with the single slit being perpendicular on the ion beam direction, would project a 1-D image of the ion beam.

In some embodiments, the material of the multi-slit knife-edge collimator 105 comprises a high density, high atomic number material. For example, the material of the multi-slit knife-edge collimator 105 may comprise tungsten, a tungsten alloy, or lead. In some embodiments, a thickness of the multi-slit knife-edge collimator 105 is about 5 centimeters (cm) or greater. In some embodiments, a thickness of the multi-slit knife-edge collimator 105 is about 1.5 cm to 12.7 cm, 2.5 cm to 12.7 cm, or about 7.6 cm. These thicknesses may allow for the attenuation of high-energy gamma ray photons.

Several factors can be considered in the design of the multi-slit knife-edge collimator 105, particularly with respect to the positions and orientations of the slits:

Photon penetration. In some embodiments, the separation of knife-edge slits is large enough to reduce or to minimize photon transmission through parts of the multi-slit knife-edge collimator that are meant to be opaque for gamma ray energies emitted along the path of an ion beam. In some embodiments, most of the gamma ray energies are above about 1.5 MeV. In some embodiments, a tungsten collimator thickness of about 7.5 cm attenuates the gamma ray beam flux by about 95%, which may be suitable for imaging.

Projection completeness. Each point along the beam path may be projected by multiple slits which cover a large range of angles. The angles of a slit can range from 0° to 90° with respect to the ion beam direction. A more uniform coverage of angles allows a better reconstruction of a 2-D image. Projection angles at or closer to 0° rather than 90° may be more important, as this allows for measurements of the distal position of the Bragg peak. A prototype was built using knife edge slits oriented at 0°, 30°, 45°, 60°, −60°, −45°, −30° with respect to the ion beam direction.

Projection overlap minimization. Because the opening angle of a knife-edge slit is limited, a small section of the image space will be in the field of view of each knife-edge edge slit. In some embodiments, the arrangement of the knife-edge slits reduces or minimizes the overlap of projections from points at different positions along the ion beam path. In some embodiments, the separation between consecutive parallel slits is chosen so that all the points along the beam path are in the full field of view of the same number of parallel knife edge slits. This helps to ensure a uniform imaging sensitivity along the whole beam path. In some embodiments, when the distance from the beam axis to the center of the collimator is equal to the distance from the center of the collimator to the position sensitive detectors, this spacing between slits may also help to reduce of to insure a minimum overlap of projections created by those slits. A prototype was built in which the parallel slits were spaced in such a manner. In this prototype, no point along the path of the beam was in the full field of view of two consecutive parallel slits. This condition was achieved for a pre-defined stand-off distance between the center of the collimator and the ion beam direction. If distances longer than such pre-defined distances are required by the application, the parallel knife-edge slits will still cover the beam path properly, although at reduced magnifications. However, for shorter distances, the parallel knife edge slits may not have all the beam path in their field of view.

In some embodiments, the position sensitive detector 110 comprises a high efficiency position sensitive detector. In some embodiments, the position sensitive detector 110 comprises a scintillator or a semiconductor detector that has a specific position resolution and a specific granularity. For example, the position sensitive detector 110 may comprise an array of bismuth germinate (BGO) crystals, an array of lutetium oxyorthosilicate (LSO) crystals, or an array of cadmium zinc telluride (CZT) detectors.

In some embodiments, the motor 125 is operable to change the position of the multi-slit knife-edge collimator 105 and the position sensitive detector 110 with respect to a surface of the target. For example, in some embodiments, the motor does not change the distance of the multi-slit knife-edge collimator 105 and the distance of the position sensitive detector 110 with respect to the surface of the target, but instead changes the position of the multi-slit knife-edge collimator 105 and the position of the position sensitive detector 110 with respect to the surface of the target 120. For example, the position of a Bragg peak in the target 120 may be determined, and then the position of the multi-slit knife-edge collimator 105 and the position of the position sensitive detector 110 with respect to a surface of the surface of the target 120 may be adjusted with the motor 125 to center the position the Bragg peak on the position sensitive detector 110 or to other adjust the gamma rays being imaged.

In some embodiments, the system 100 (i.e., including the multi-slit knife-edge collimator 105 and the position sensitive detector 110) is configured to be moved and positioned at different angles around the target 120. In some embodiments, two or more systems 100 are positioned at different angles around the target 120. Such configurations may allow for the generation of multiple 2-D images, with the images being generated at different angles with respect to the sample 120. The 2-D images may be combined into a 2-D distribution using analytical or iterative image reconstruction algorithms.

Image reconstruction algorithms can be used to generate a 2-D image of the distribution of gamma rays emitted along the ion beam path. The 2-D image generation can be performed using a computing device that acquires and processes data generated by the position sensitive detector 110. For example, such image reconstruction algorithms include Expectation-Maximization Maximum Likelihood approaches, filtered back-projection approaches, and compressive sensing approaches. The relative geometric simplicity of the gamma ray source distribution along the ion beam path and the presence of a low image background (e.g., especially at gamma ray energies above 1.5 MeV) may allow for high fidelity image reconstruction. In some embodiments, a 2-D image of the distribution of gamma rays can be generated every about 17 milliseconds (ms). In some embodiments, two or more 2-D images are combined to generate a three dimensional (3-D) image. In some embodiments, a single 1-D image along the beam path is reconstructed.

In some embodiments, a system controller is employed to operate the ion beam therapy dose verification system. The controller will typically include one or more memory devices and one or more processors. The processor may include a CPU or computer, analog and/or digital input/output connections, controller boards, etc. The controller may control all of the activities of the ion beam therapy dose verification system. The system controller executes system control software including sets of instructions for controlling data collection. Other computer programs stored on memory devices associated with the controller may be employed in some embodiments.

In some embodiments, the system controller may be coupled to the system controller of the ion beam system used to generate the ion beam. In such a system, the dose of ions can be determined with the ion beam therapy dose verification system and this information can be used to control the ion beam system. For example, from an analysis of information generated by the ion beam therapy dose verification system, the controller of the ion beam system may modify or stop the ion beam when the measured distribution of the gamma ray sources does not correspond with the intended location for ion beam dose deposition.

Typically there will be a user interface associated with the controller. The user interface may include a display screen, graphical software displays of the system and/or operating parameters, and user input devices such as pointing devices, keyboards, touch screens, microphones, etc.

The computer program code for controlling the data collection and related processes in a process sequence can be written in any conventional computer readable programming language; for example, assembly language, C, C++, Pascal, Fortran or others. Compiled object code or script is executed by the processor to perform the tasks identified in the program.

In some embodiments, an ion beam therapy dose verification system is used with an imaging system that is used to determine the location of an organ or a feature in a human or animal body. For example, the imaging system may be an x-ray system or an ultrasound system. The imaging system can be used to direct the ion beam (and its associated Bragg peak) at a feature in the body and account for any shifts of the feature in the body. For example, an organ with a tumor that is to be radiated with the ion beam may shift in the human body. The imaging system can be used to help insure the Bragg peak of the ion beam is at the position of tumor. For example, an image of the gamma rays generated by the ion beam can be overlaid on an image generated with the imaging system and the dose to different portions of a body can be determined.

Figure 2A:
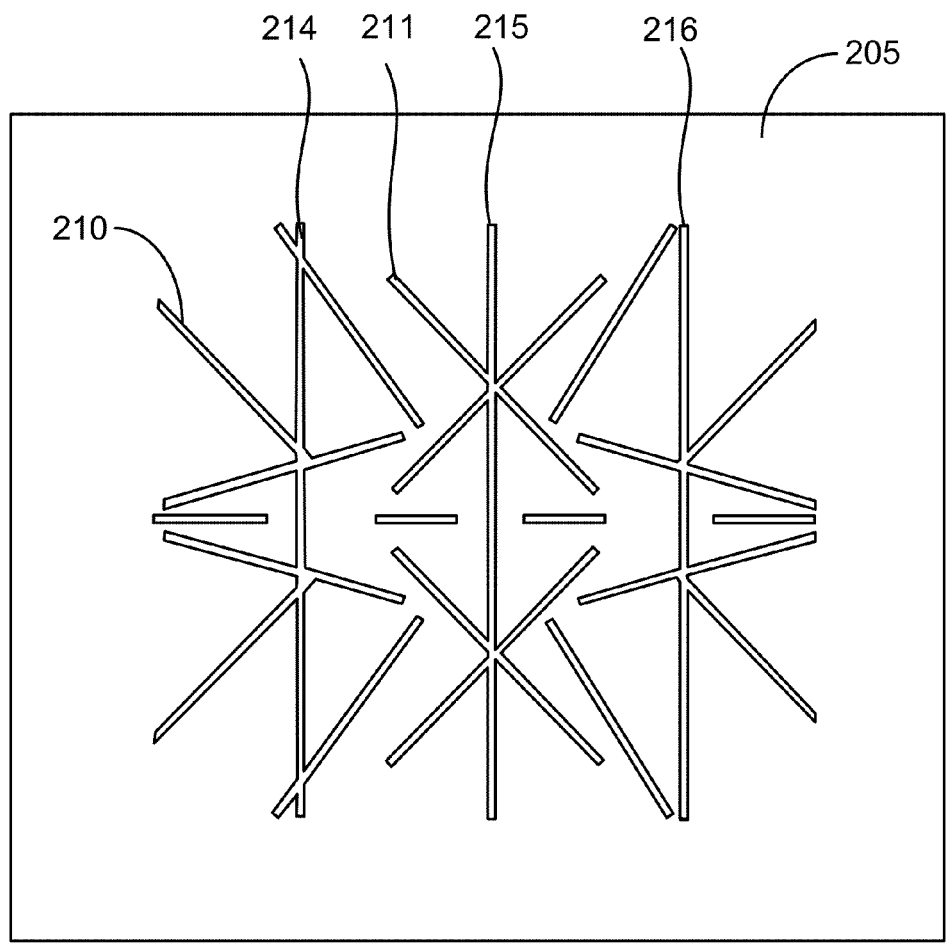
FIGS. 2A and 2B show examples of a schematic illustrations of multi-slit knife-edge collimators having a pattern of knife-edge slits.
Figure 2B:
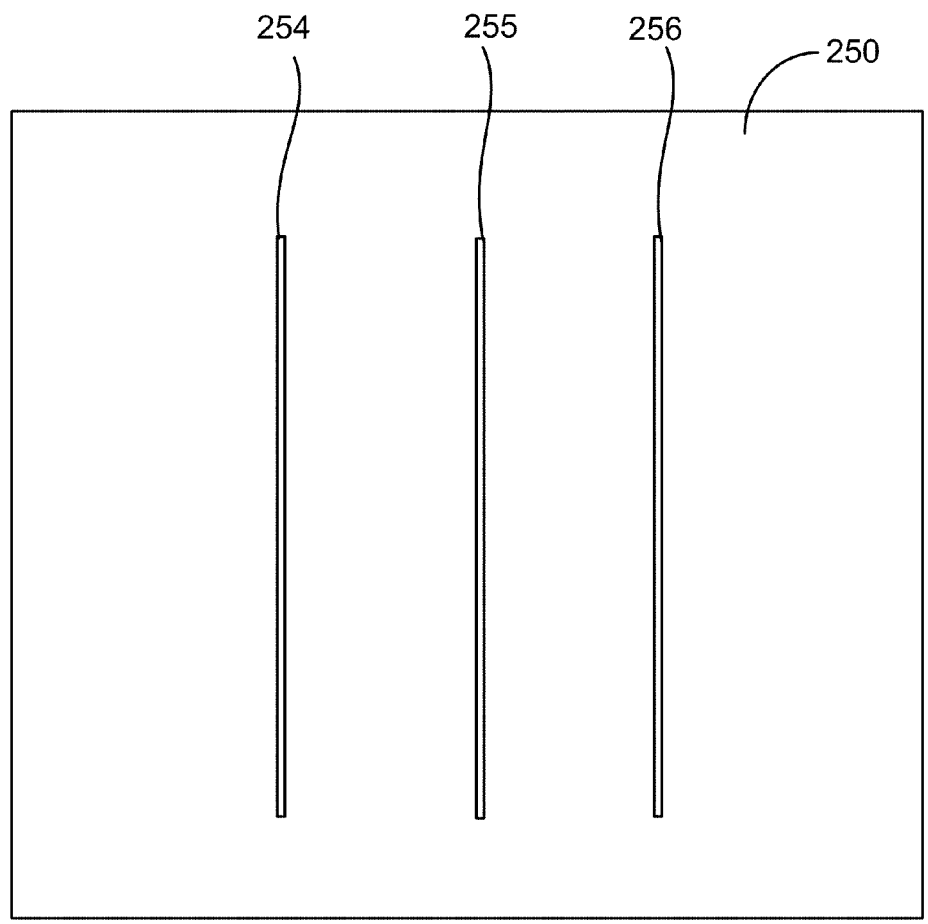

FIGS. 2A and 2B show examples of schematic illustrations of multi-slit knife-edge collimators having a pattern of knife-edge slits. The multi-slit knife-edge collimator 105 shown in FIG. 1 is a cross-sectional view of a collimator, and the multi-slit knife-edge collimator 205 shown in FIG. 2A is a top-down view of a collimator. The pattern of knife-edge slits in the multi-slit knife-edge collimator 205 shown in FIG. 2A may be specified to image the path of the ion beam 115 shown in FIG. 1. In some embodiments, dimensions of the multi-slit knife-edge collimator 205 as shown in FIG. 2A are about 4 inches by 4 inches to about 12 inches by 12 inches, or about 8 inches by 8 inches. While the multi-slit knife-edge collimator 205 is shown a having a square shape, a collimator may be rectangular or have another shape.

The multi-slit knife-edge collimator 205 includes a plurality of knife-edge slits. Knife-edge slits of the plurality of knife-edge slits may have different lengths and may be at disposed at different angles with respect to one another. For example, the multi-slit knife-edge collimator 205 includes a first plurality of knife-edge slits 214, 215, and 216 that are substantially parallel to one another. In some embodiments, substantially parallel means that the slits are parallel to one another within 1°. The multi-slit knife-edge collimator 205 also includes a second plurality of knife-edge slits 210 and 211 that are substantially parallel to one another. In some embodiments, the first plurality knife-edge slits is not parallel to the second plurality of knife-edge slits. Stated in a different manner, in some embodiments there is an angle (i.e., an angle greater than 0°) between knife-edge slits of the first plurality of knife-edge slits and knife-edge slits of the second plurality of knife-edge slits.

In some embodiments, at least one of the slits of the first plurality of knife-edge slits intersects with at least one of the slits of the second plurality of knife-edge slits. As shown in FIG. 2A, slit 211 intersects with slit 215.

Turning to FIG. 2B, the multi-slit knife-edge collimator 250 shown is a top-down view of a collimator. The pattern of knife-edge slits in the multi-slit knife-edge collimator 250 shown in FIG. 2B may be specified to image the path of the ion beam 115 shown in FIG. 1. In some embodiments, dimensions of the multi-slit knife-edge collimator 250 as shown in FIG. 2B are about 4 inches by 4 inches to about 12 inches by 12 inches, or about 8 inches by 8 inches. While the multi-slit knife-edge collimator 250 is shown a having a square shape, a collimator may be rectangular or have another shape.

The multi-slit knife-edge collimator 250 includes a plurality of knife-edge slits 254, 255, and 256 that are substantially parallel to each other. In some embodiments, substantially parallel means that the slits are parallel to one another within 1°. In some embodiments, the multi-slit knife-edge collimator 250 includes 2, 3, 4, 5, 6 or more knife-edge slits that are substantially parallel to each other. In some embodiments, the multi-slit knife-edge collimator 250 only includes knife-edge slits that are substantially parallel to each other.

Figure 3A:
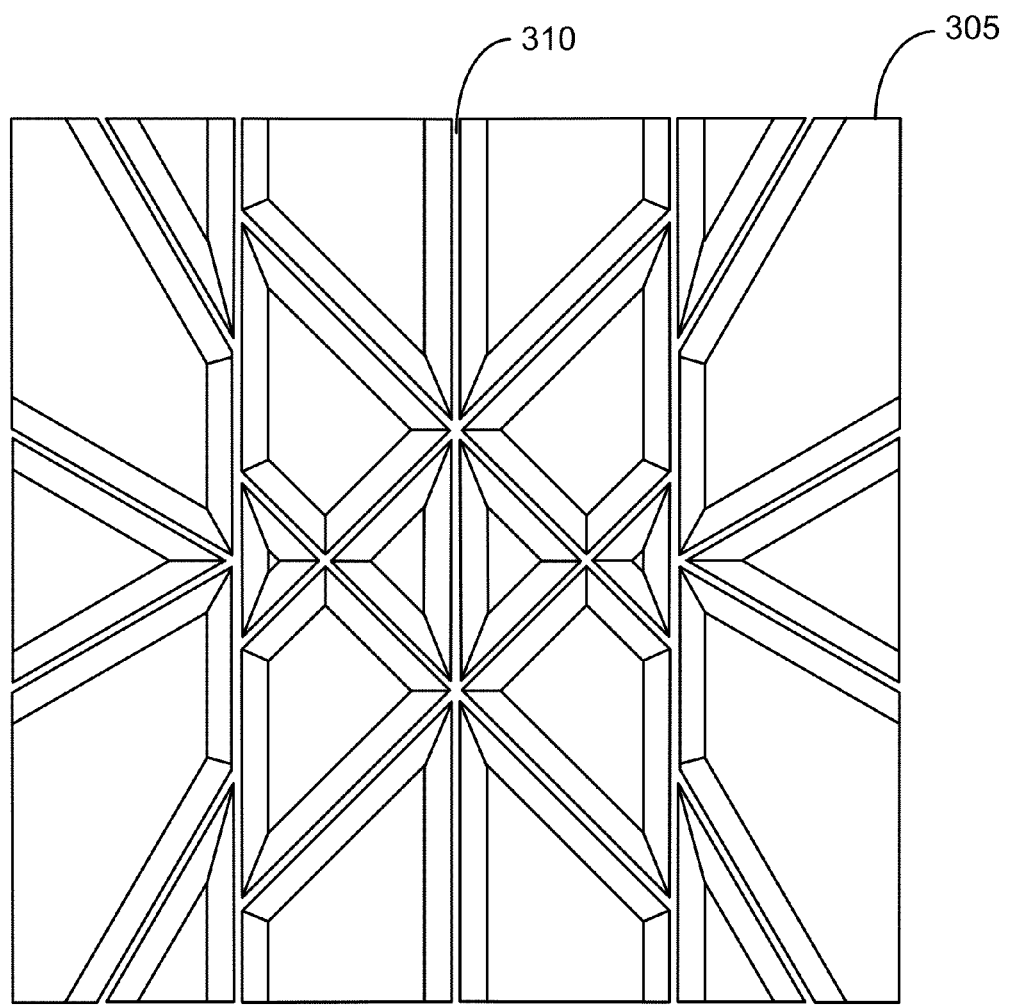
FIGS. 3A and 3B show examples of schematic illustrations of a multi-slit knife-edge collimator having a pattern of knife-edge slits.
Figure 3B:
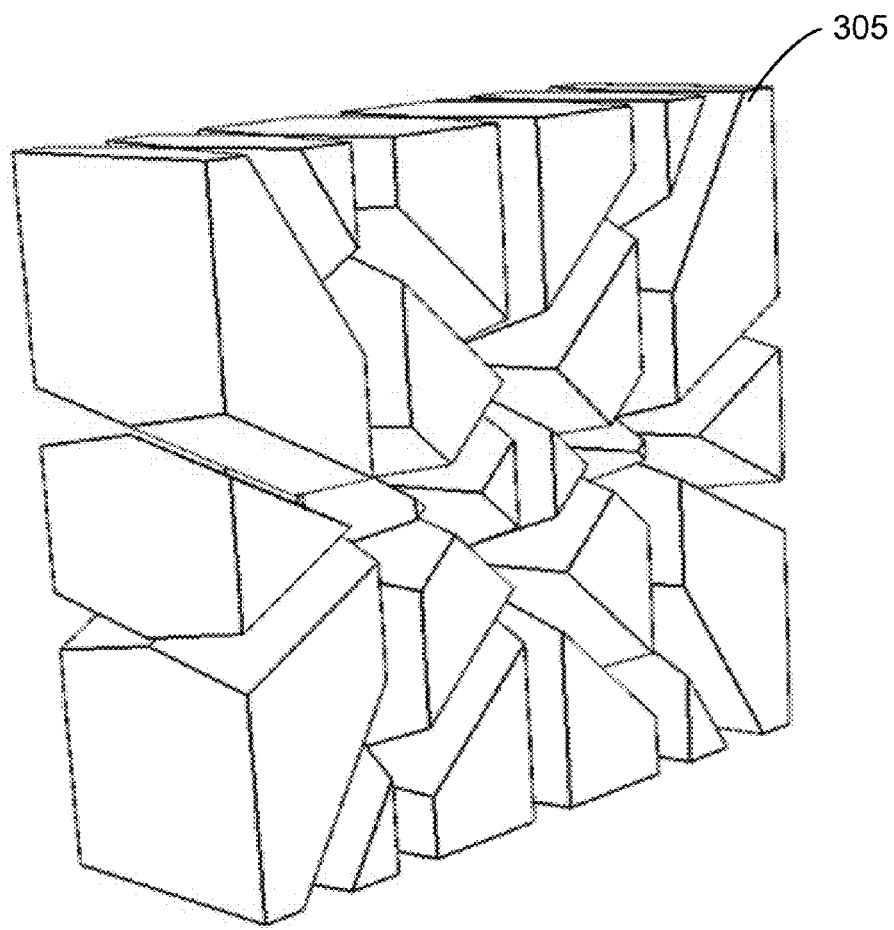

FIGS. 3A and 3B show examples of schematic illustrations of a multi-slit knife-edge collimator having a pattern of knife-edge slits. FIG. 3A shows an example of a top-down view of a multi-slit knife-edge collimator 305. FIG. 3B shows an example of an isometric illustration of the multi-slit knife-edge collimator 305. As shown in FIGS. 3A and 3B, the multi-slit knife-edge collimator 305 includes a plurality of knife-edge slits, including slit 310. The multi-slit knife-edge collimator 305 includes a first knife-edge slit that intersects with a second knife-edge slit. The multi-slit knife-edge collimator 305 also include a first plurality of knife-edge slits that are substantially parallel to one another and a second plurality of knife-edge slits that are substantially parallel to one another, with the first plurality of knife-edge slits not being parallel to the second plurality of knife-edge slits.

Figure 4:
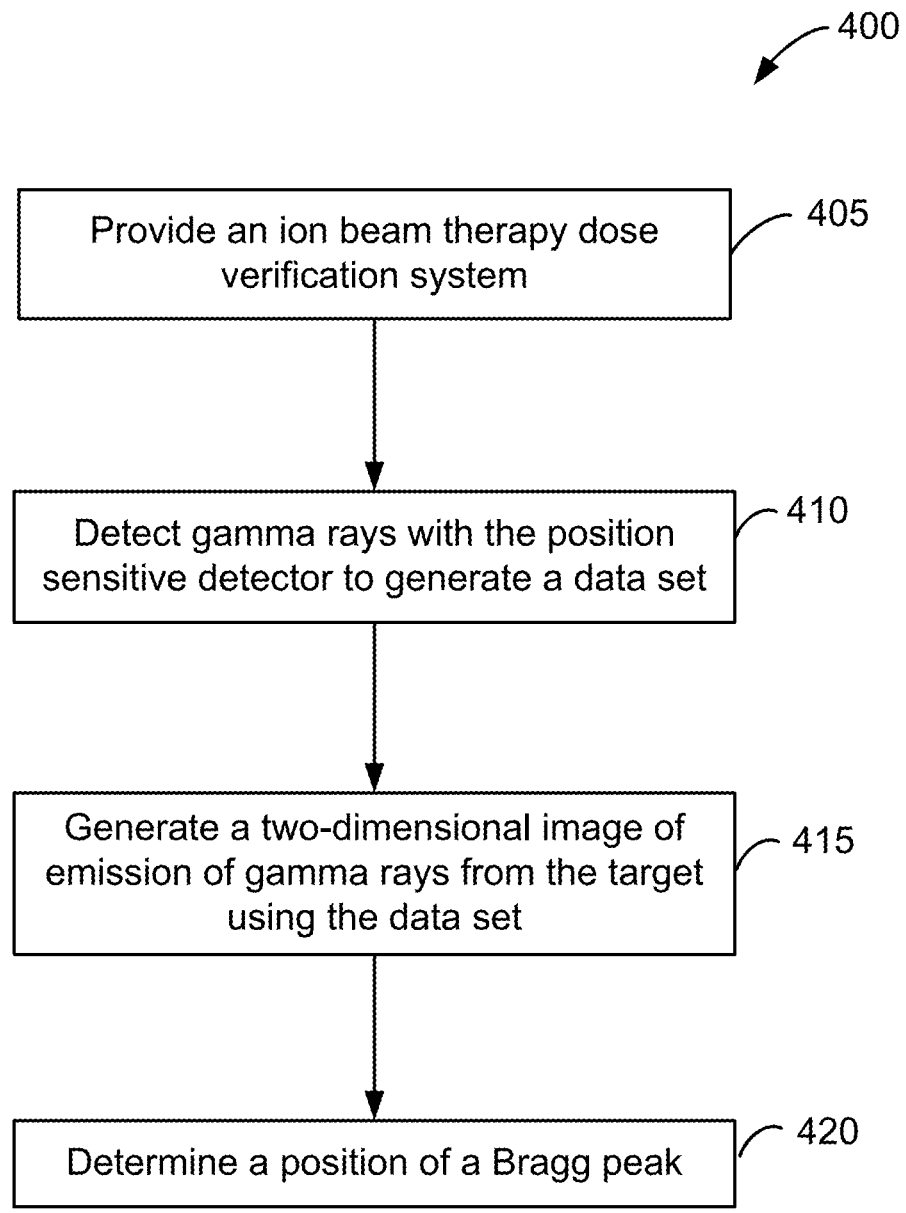
FIG. 4 shows an example of a flow diagram illustrating the use of an ion beam therapy dose verification system.

FIG. 4 shows an example of a flow diagram illustrating the use of an ion beam therapy dose verification system. Starting at block 405 of the process 400, an ion beam therapy dose verification system is provided. The system includes a position sensitive detector and a collimator. The position sensitive detector is configured to detect gamma rays generated by an ion beam interacting with a target. The collimator is positioned between the target and the position sensitive detector. The collimator may be any of the multi-slit knife-edge slits described herein. The system may be, for example, the system 100 shown in FIG. 1 or any of the other systems described herein.

At block 410, gamma rays are detected with the position sensitive detector to generate a data set. For example, when an ion beam impinges on a target, gamma rays are emitted from nuclear reactions of the ion beam with the target or by the scattering of the ion beam along the path of the ion beam. In some embodiments, the ion beam has an energy of 10 MeV to 260 MeV, about 60 to 180 MeV, or about 120 MeV. In some embodiments, the gamma rays generated by the interaction of the ion beam with the target have an energy of about 0.05 MeV to 10 MeV or about 2 MeV to 6 MeV.

At block 415, a two-dimensional image of emission of gamma rays from the target is generated using the data set. For example, to generate a two-dimensional image of the emission of gamma rays from the target, matrix calculations involving the system response of the ion beam therapy dose verification system and the data set can be performed. Image reconstruction algorithms, known to one having ordinary skill in the art, can be used to generate the two-dimensional image of the gamma ray emissions. For example, iterative algorithms, such as Expectation Maximization-Maximum Likelihood, or analytical algorithms, such as filtered back-projection, can be used.

The system response of the ion beam therapy dose verification system depends on the pattern of knife-edge slits in the collimator. The system response includes information regarding how much a gamma ray emitted from each point in the target is attenuated by the collimator before impinging the position sensitive detector. The system response includes this information for each point on the target to be imaged and each point on the position sensitive detector. In some embodiments, the system response also includes information regarding the probability that a gamma ray will generate a signal at each point on the position sensitive detector.

In some embodiments, the data set is processed before generating the two-dimensional image to remove noise and other artifacts in the data. In some embodiments, the two-dimensional image is displayed on a computer screen or other display.

At block 420, a position of the Bragg peak of the ion beam is determined. Using the two-dimensional image of emission of gamma rays from the target, a maximum position of gamma ray emission can be determined. This maximum position of gamma ray emission corresponds to the Bragg peak.

In some embodiments, different images of the emission of gamma rays can be generated. For example, in some embodiments, at block 415, a one-dimensional (1-D) image of emission the gamma rays from the target is generated by constraining the solution of the image reconstruction problem to the direction of the ion beam.

In some embodiments, after determining a position of a Bragg peak of the ion beam at lock 420, the positions of the position sensitive detector and the collimator are moved so that the Bragg peak is proximate a center of the position sensitive detector. In some embodiments, the positions of the position sensitive detector and the collimator are moved to otherwise adjust the position of the Bragg peak or the gamma rays being imaged on the position sensitive detector. In some embodiments, operations 405 through 420 are then performed again.

The embodiments described above of a system including a multi-slit knife-edge collimator having intersecting knife-edge slits may be used for imaging the majority of an extended beam path inside a target. In some instances, a multi-slit knife-edge collimator having substantially parallel slits perpendicular to the ion beam direction may be more suitable for imaging short beam paths inside a target. In some instances, a multi-slit knife-edge collimator having substantially parallel slits perpendicular to the ion beam direction may be more suitable for imaging longer paths inside a target when the collimator is used with a motorized system that is functionally connected to a beam delivery system. In such an embodiment, the collimator and the position sensitive detector are positioned so that the expected position of the Bragg peak is substantially in the middle of the field of view of the system. Because knife-edge slits perpendicular to the beam path provide projections that are the most suitable for determining the distal position of the Bragg peak, a plurality of knife-edge slits perpendicular to the beam path will increase the imaging sensitivity.

Figure 5:
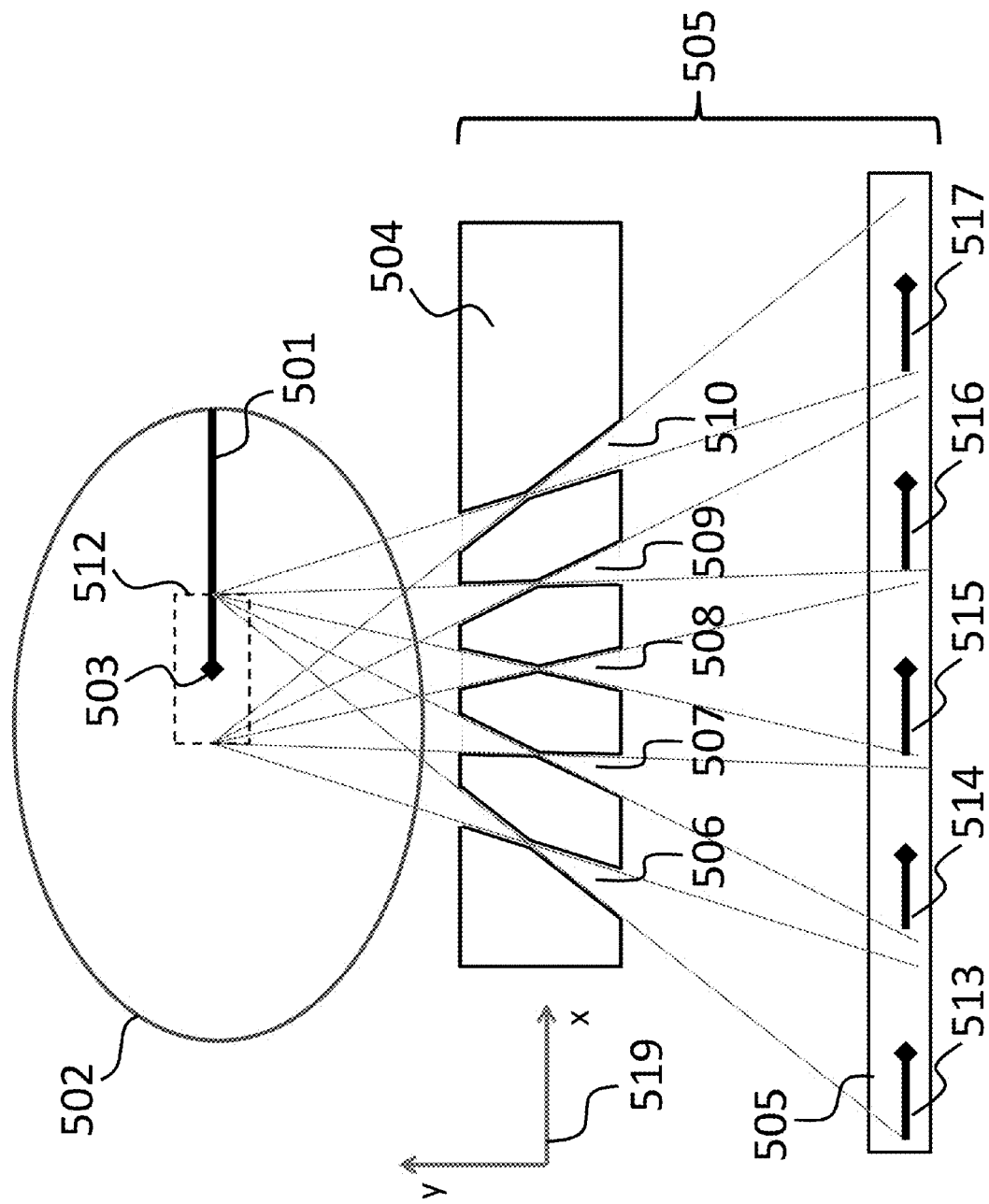
FIG. 5 shows an example of a schematic illustration of an ion beam therapy dose verification system.

FIG. 5 shows an example of a schematic illustration of an ion beam therapy dose verification system. As shown in FIG. 5, the ion beam therapy dose verification system 500 comprises a collimator 504 and a position sensitive detector 505. The collimator 504 includes a plurality of knife-edge slits 506, 507, 508, 509 and 510. In some embodiments, the plurality of knife-edge slits are substantially parallel to one another. Also shown in FIG. 5 are an ion beam path 501 and a target 502. Most of the dose of the ion beam occurs at the end of the ion beam path 501 at a Bragg peak 503. The collimator is disposed between the target 502 and the position sensitive detector 505. The plurality of knife-edge slits 506, 507, 508, 509, and 510 are defined in the collimator 504 in a manner so that an expected position of the Bragg peak 503 is contained in the field of view 512 of the plurality of knife-edge slits 506, 507, 508, 509, and 510.

In some embodiments, the plurality of knife-edge slits 506, 507, 508, 509, and 510 cast projections on the position sensitive detector 505 that overlap, partially overlap, or be separated. In some embodiments, better imaging performance is expected when the projections are separated. The part of the ion beam path 501 in the field of view 512 of the plurality of knife-edge slits will be projected onto the position sensitive detector 505 at locations 513, 514, 515, 516, and 517.

The presence of multiple slits in the collimator 504 increases the imaging sensitivity of the system 505. In some embodiment, the collimator 504 is designed so that no other part of the ion beam path 501 outside the field of view of the plurality of knife-edge slits 512 is un-collimated with respect to the detector 505.

In some embodiments, the detector 505 is 1-D, 2-D, or 3-D position sensitive. In some embodiments, the detector 505 is a single detector or an array of detectors. For an array of detectors, individual detectors can be co-planar (as shown in FIG. 5) or can be arranged at different angles. For example, the detectors can be arranged to face the openings of the plurality of knife-edge slits normally, so that projection 513 will be perpendicular to the line connecting the detector detecting projection 513 and slit opening 506, projection 514 will be perpendicular to the line connecting the detector detecting projection 514 and slit opening 507, and so on.

The field of view 512 of the plurality of knife-edge slits may include the expected position of the Bragg peak 503 and some area around the expected position of the Bragg peak. The area around the expected position of the Bragg peak may allow for the ion beam therapy dose verification system 500 to show an intensity decrease of gamma rays from the Bragg peak after the Bragg peak. This may help the system 500 provide the position of the Bragg peak with high accuracy.

Because the field of view 512 of the plurality of knife edge slits may be small to allow for improved imaging sensitivity in a region, in order to accommodate ion beams of various track lengths and positions, the collimator 504 can be moved along the distal direction of the ion beam (x-direction in coordinate system 519) in response to the expected movement of the Bragg peak 503 during the ion treatment.

Other patterns of knife-edge slits in the collimator 504 (i.e., the plurality of knife edge slits not being substantially parallel to one another) are also possible. For example, in some embodiments, knife-edge slits of the plurality of knife-edge slits are positioned on the surface of a virtual circle, with the center of the circle placed close to the field of view 512. In such a configuration, the knife-edge slits may all have a geometry similar to knife-edge slit 508.

Other approaches to imaging gamma rays emitted during proton beam treatment have been proposed or tested. These include: single knife-edge slit collimators (e.g., which generate a 1-D image of the beam) [7, 8], 1-0 parallel slit collimators [9], and Compton cameras [10, 11]. According to some estimates, single knife-edge collimators can provide a good combination of sensitivity and position resolution, with a $4*10^{-4}$ detection sensitivity and 6 millimeter (mm) position resolution in the distal direction; the incident energy of the proton beam was 120 MeV.

According to Monte Carlo simulations, the systems described with respect to FIGS. 1-3B can provide a much more complete and accurate representation of the proton beam and the associated Bragg peak at comparable proton beam energies. The Bragg peak is a peak on the Bragg curve; a Bragg curve plots the energy loss of the ion beam as it travels though the target.

For example, for a 150 MeV proton beam, the detection sensitivity for the detection of gamma rays above 1.5 MeV was $3.5*10^{-3}$. The imaging position resolution was 2.7 mm FWHM for a gamma ray source situated on the normal direction above a multi-slit knife-edge collimator. An image resolution of around 1.8 mm FWHM was obtained when the source was positioned at 5 to 10 degrees off the normal direction above the multi-slit knife-edge collimator. These values represent a factor of 8.75 increase in sensitivity and a factor of 3 increase in resolution when compared to the single knife-edge slit collimator design described in Reference 7.

However, imaging resolution and detection sensitivity do not characterize the capability of the imaging system to accurately provide the distal position of the Bragg peak. A Linear Discriminant Analysis was used to determine how well the systems described with respect to FIGS. 1-3B were able to capture differences in the projected images when the Bragg peak of a proton beam is distally shifted by 1 mm. The linear discriminant for a single knife-edge slit collimator was calculated to be S=31 for $10^8$ incident number of protons. For the multi-slit knife-edge collimators, the linear discriminant is S=750 for the same number of incident protons. This high discrimination may allow the system to provide the position of the Bragg peak with an integration time of a few seconds. This level of performance may allow for real-time dose distribution characterization and beam adjustment in close to real time.

While the embodiments described herein have been described as being implemented to generate dose distribution information for radiation therapy using ion beams, the proposed combination of a multi-slit knife-edge collimator and a position sensitive detector coupled to an image reconstruction algorithm can be used for many different applications involving imaging of sources of high-energy gamma rays. For example, the embodiments described herein could be used to characterize and diagnose materials by active interrogation using gamma rays, hard X-rays, neutrons, or other beams.

Conclusion

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

REFERENCES

The following references are herein incorporated by reference:
1. Dieter Schardt et al. "Heavy-ion tumor therapy: Physical and radiobiological benefits", REVIEWS OF MODERN PHYSICS, VOLUME 82, (2010) pp. 383.
2. Parodi K, Enghardt W, and Haberer T, "In-beam PET measurements of positron radioactivity induced by proton beams" Phys. Med. Biol. 46 (2002) 21-36.
3. R. Accorsi, F. Gasparini, and R. C. Lanza, "Optimal coded aperture patterns for improved SNR in nuclear medicine imaging", Nuclear Instruments & Methods in Physics Research Section a-Accelerators Spectrometers Detectors and Associated Equipment 474, 273-284 (2001).
4. K. A. Nugent, "Coded Aperture Imaging—a Fourier Space Analysis", Applied Optics 26, 563-569 1987.
5. K. Choi and D. J. Brady, "Coded aperture computed tomography", Proc. of SPIE 7468, 74680B1-74680B10 (2009).
6. R. F. Marcia and R. M. Willett, "Compressive coded aperture superresolution image reconstruction", IEEE International Conference on Acoustics, Speech and Signal Processing, ICASSP 2008 833-836 (2008).
7. V. Born, L. Joulaeizadeh, and F. Beekman, "Real-time prompt gamma monitoring in spot-scanning proton therapy using imaging through a knife-edge-shaped slit", Phys Med Biol. 57, 297-308 (2012).
8. J. Smeets, F. Roellinghoff, D. Prieels, F. Stichelbaut, A. Benilov, P. Busca, e. Fiorini, R Peloso, M. Basilavecchia, T. Frizzi, J. e. Dehaes, and A. Dubus, "Prompt gamma imaging with a slit camera for real-time range control in proton therapy", Phys Med Biol. 57,3371-405 (2012).
9. C. H. Min, H. R. Lee, C. H. Kim, and S. B. Lee, "Development of array-type prompt gamma measurement system for in vivo range verification in proton therapy", Med Phys 39, 2100-7 (2012).
10. M. Frandes, A. Zoglauer, V. Maxim, and R. Prost, "A Tracking Compton-Scattering Imaging System for Hadron Therapy Monitoring", IEEE Transactions on Nuclear Science 57, 144-150 (2010).
11. S. Kurosawa, H. Kubo, K. Veno, S. Kabuki, S. Iwaki, M. Takahashi, K. Taniue, N. Higashi, K. Miuchi, T. Tanimori, D. Kim, and J. Kim, "Prompt gamma detection for range verification in proton therapy", Current Applied Physics 12, 364-368 (2012).

What is claimed is:

1. A system comprising:
a position sensitive detector configured to detect gamma rays generated by an ion beam interacting with a target; and
a collimator positioned between the target and the position sensitive detector, the collimator including a first plurality of knife-edge slits and a second plurality of knife-edge slits, the first plurality of knife-edge slits being substantially parallel to one another, the second plurality of knife-edge slits being substantially parallel to one another, the first plurality of knife-edge slits not being parallel to the second plurality of knife-edge slits, a first knife-edge slit of the first plurality of knife-edge slits intersecting with a first knife-edge slit of the second plurality of knife-edge slits at an angle other than 90°.

2. The system of claim 1, wherein the ion beam comprises ions selected from a group consisting of protons and carbon ions.

3. The system of claim 1, wherein the collimator is about 1.5 centimeters to 12.7 centimeters thick.

4. The system of claim 1, wherein the collimator comprises tungsten.

5. The system of claim 1, wherein the gamma rays have energies of about 0.05 MeV to 10 MeV.

6. The system of claim 1, further comprising:
a motor, wherein the motor is coupled to the position sensitive detector and the collimator, and wherein the motor is operable to change a position of the position sensitive detector and the collimator with respect to a surface of the target.

7. The system of claim 1, wherein at least one of the first plurality of knife-edge slits forms an angle with respect to the ion beam with the angle being selected from a group consisting of −60°, −45°, −30°, 0°, 30°, 45°, and 60°.

8. The system of claim 1, wherein an angle of a knife edge slit of the first plurality of knife-edge slits is about 5° to 35°.

9. A method comprising:
providing a system including:
a position sensitive detector configured to detect gamma rays generated by an ion beam interacting with a target; and
a collimator positioned between the target and the position sensitive detector, the collimator including a first plurality of knife-edge slits and a second plurality of knife-edge slits, the first plurality of knife-edge slits being substantially parallel to one another, the second plurality of knife-edge slits being substantially parallel to one another, the first plurality of knife-edge slits not being parallel to the second plurality of knife-edge slits, a first knife-edge slit of the first plurality of knife-edge slits intersecting with a first knife-edge slit of the second plurality of knife-edge slits at an angle other than 90°;

detecting the gamma rays with the position sensitive detector to generate a data set; and generating a two-dimensional image of emission of the gamma rays from the target with calculations using the data set.

10. The method of claim 9, wherein the ion beam comprises ions selected from a group consisting of protons and carbon ions.

11. The method of claim 9, wherein the collimator is about 1.5 centimeters to 12.7 centimeters thick.

12. The method of claim 9, wherein the collimator comprises tungsten.

13. The method of claim 9, wherein the gamma rays have energies of about 0.05 MeV to 10 MeV.

14. The method of claim 8, further comprising:

after determining the position of a Bragg peak of the ion beam, moving the position of the position sensitive detector and the collimator so that the Bragg peak is proximate a center of the position sensitive detector.

15. The method of claim 9, wherein at least one the plurality of knife-edge slits forms an angle with respect to the ion beam with the angle being selected from a group consisting of −60°, −45°, −30°, 0°, 30°, 45°, and 60°.

16. The method of claim 9, wherein the generating the two-dimensional image of emission of the gamma rays from the target with calculations using the data set further uses a system response, and wherein the system response includes information regarding the amount a gamma ray emitted from each point in the target is attenuated by the collimator before being detected with the position sensitive detector.

17. The method of claim 9, wherein an angle of a knife edge slit of the first plurality of knife-edge slits is about 5° to 35°.

18. The method of claim 9, further comprising:

determining a position of a Bragg peak of the ion beam.

19. A collimator comprising:

a first plurality of knife-edge slits; and a second plurality of knife-edge slits, the first plurality of knife-edge slits being substantially parallel to one another, the second plurality of knife-edge slits being substantially parallel to one another, the first plurality of knife-edge slits not being parallel to the second plurality of knife-edge slits, a first knife-edge slit of the first plurality of knife-edge slits intersecting with a first knife-edge slit of the second plurality of knife-edge slits at an angle other than 90°.

20. The collimator of claim 19, wherein an angle of a knife edge slit of the first plurality of knife-edge slits is about 5° to 35°.

* * * * *